(12) United States Patent
Kim et al.

(10) Patent No.: US 7,595,068 B2
(45) Date of Patent: Sep. 29, 2009

(54) COMPOSITION COMPRISING NOTOGINSENG RADIX EXTRACT FOR PREVENTING AND TREATING OF ARTHRITIS AS AN EFFECTIVE INGREDIENT

(75) Inventors: Jung-Keun Kim, Seongnam-si (KR); Se-Won Kim, Cheonan-si (KR); Hyung-Gun Kim, Seoul (KR); Seon-Yle Ko, Kongju-si (KR); Jong-Yeo Kim, Cheonan-si (KR); Sunhwa Chang, Cheonan-si (KR); Dong-Heon Baek, Seoul (KR); Byung-Eui Lee, Daejeon-si (KR); Seong-Hee Ko, Gangneung-si (KR); Youngnim Choi, Seoul (KR); Dong Sik Jung, Cheonan-si (KR); Heejong Woo, Cheonan-si (KR)

(73) Assignee: Oscotec Inc., Cheonan-Si (KR)

( * ) Notice: Subject to any disclaimer, the term of this patent is extended or adjusted under 35 U.S.C. 154(b) by 0 days.

(21) Appl. No.: 12/118,276

(22) Filed: May 9, 2008

(65) Prior Publication Data

US 2008/0233217 A1 Sep. 25, 2008

Related U.S. Application Data

(62) Division of application No. 10/568,257, filed on Feb. 13, 2006, now abandoned.

(51) Int. Cl.
*A61K 36/25* (2006.01)

(52) U.S. Cl. .................................... 424/728

(58) Field of Classification Search ............. None
See application file for complete search history.

(56) References Cited

U.S. PATENT DOCUMENTS

| 5,702,728 | A * | 12/1997 | Bi ............... 424/547 |
| 6,383,525 | B1 * | 5/2002 | Hsu et al. ........... 424/728 |
| 6,884,627 | B2 * | 4/2005 | Hsu et al. ........... 436/501 |
| 2003/0143289 | A1 * | 7/2003 | Chen .............. 424/728 |

FOREIGN PATENT DOCUMENTS

| CN | 1114579 | * | 1/1996 |
| CN | 1141803 | * | 2/1997 |
| CN | 1158257 | * | 9/1997 |
| CN | 1217190 | * | 5/1999 |
| CN | 1240144 | * | 1/2000 |
| JP | 11-139979 | * | 5/1999 |

* cited by examiner

*Primary Examiner*—Christopher R. Tate
(74) *Attorney, Agent, or Firm*—Lucas & Mercanti, LLP

(57) ABSTRACT

The present invention relates to a composition comprising Notoginseng radix extract for preventing and treating arthritis as an effective ingredient.

Notoginseng radix extract of the present invention inhibits release of tumor necrosis factor-alpha (TNF-α) and is the death of activated T-cells only, so that it can be effectively used for the production of a medicine for preventing and treating arthritis and health food as well.

9 Claims, 5 Drawing Sheets

[Figure 1]
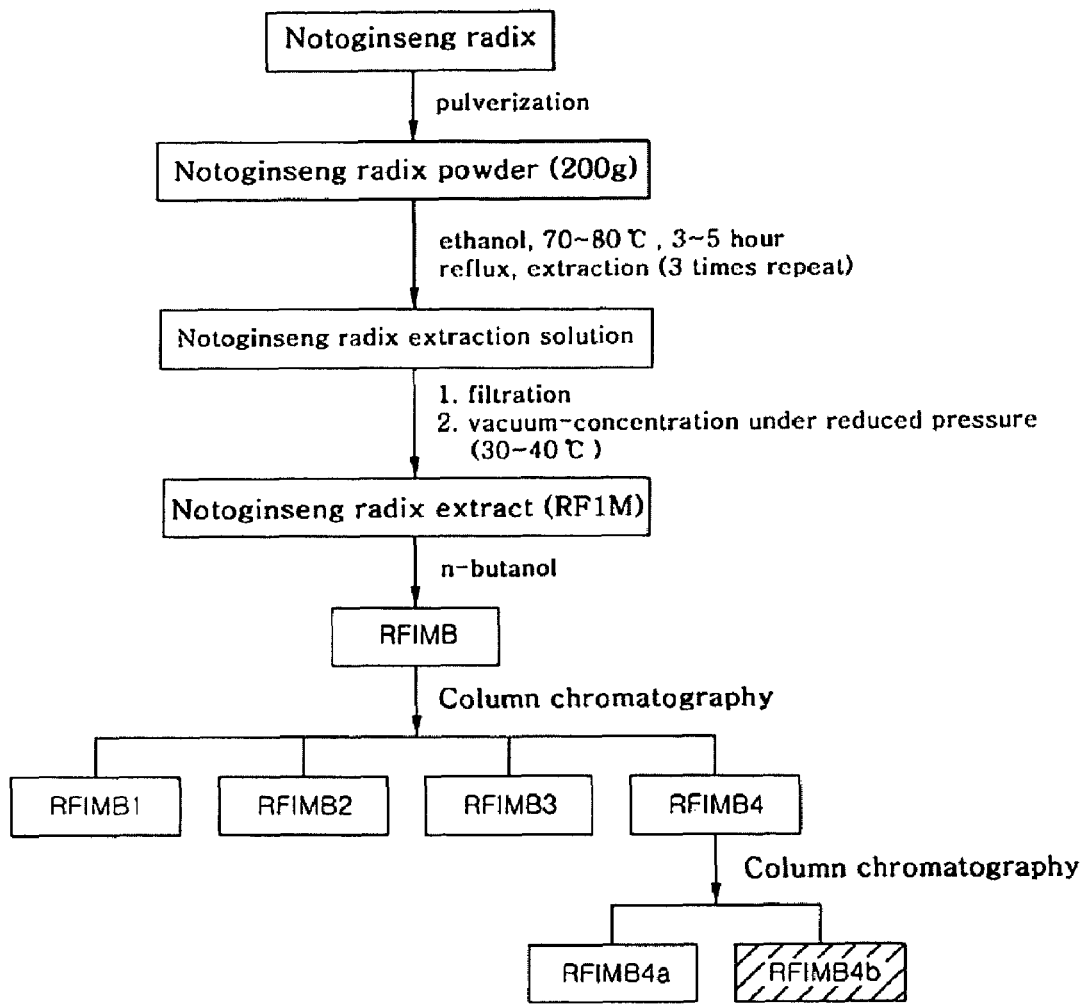

[Figure 2]
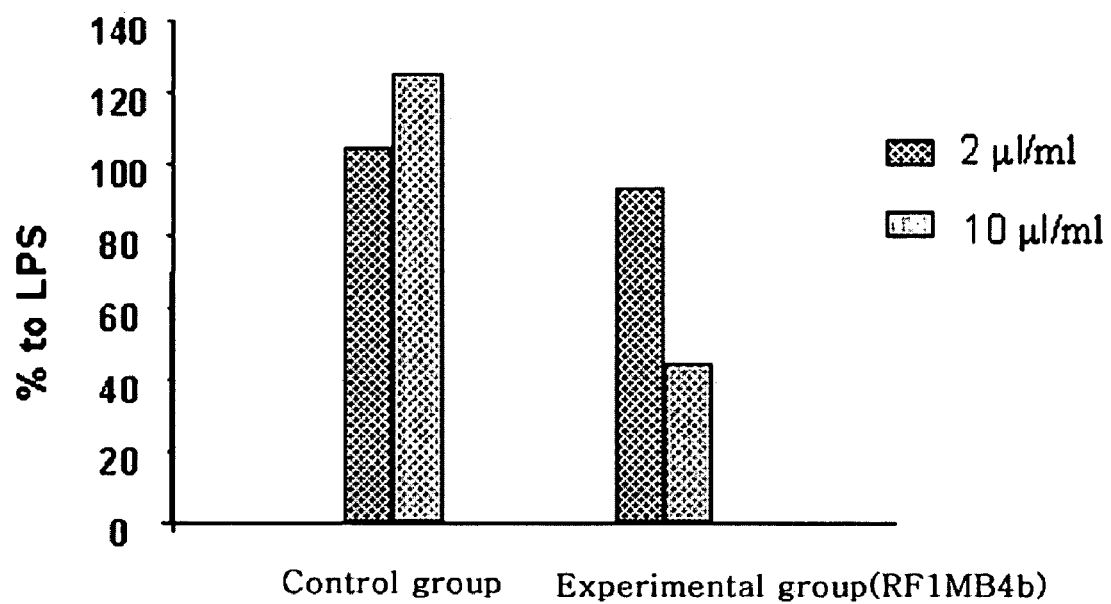

[Figure 3]
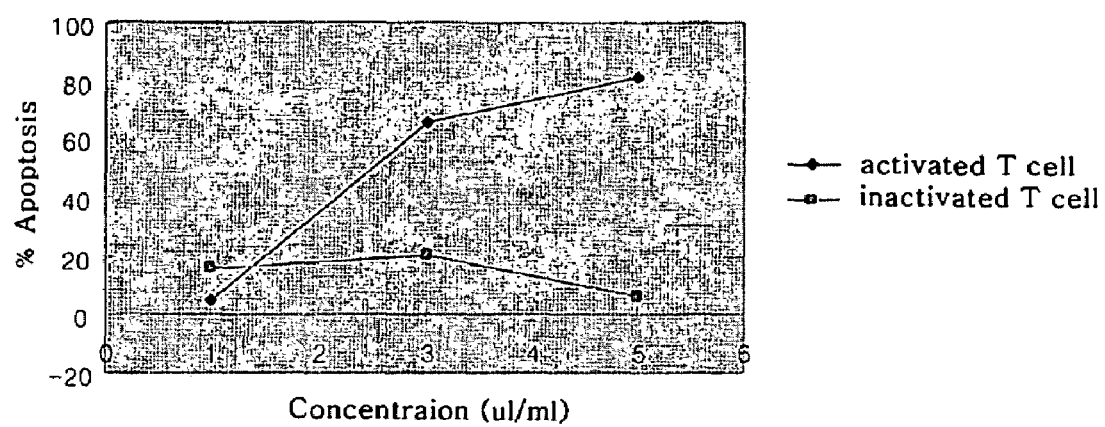

[Figure 4]
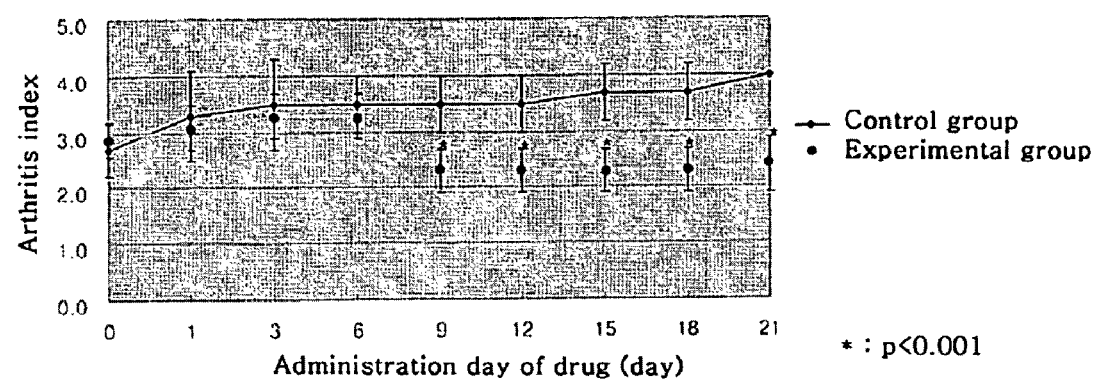

[Figure 5]
1) CIA mice without treatment of *Notoginseng radix* extract
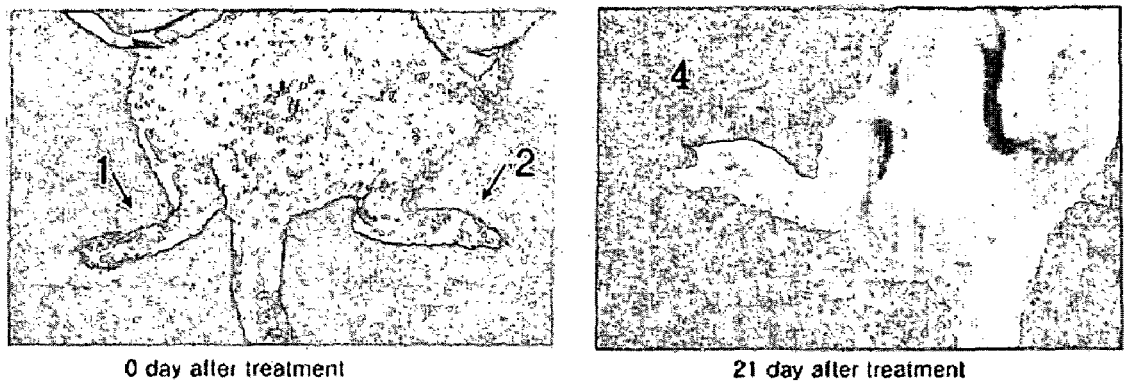
0 day after treatment        21 day after treatment
2) CIA mice with treatment of *Notoginseng radix* extract
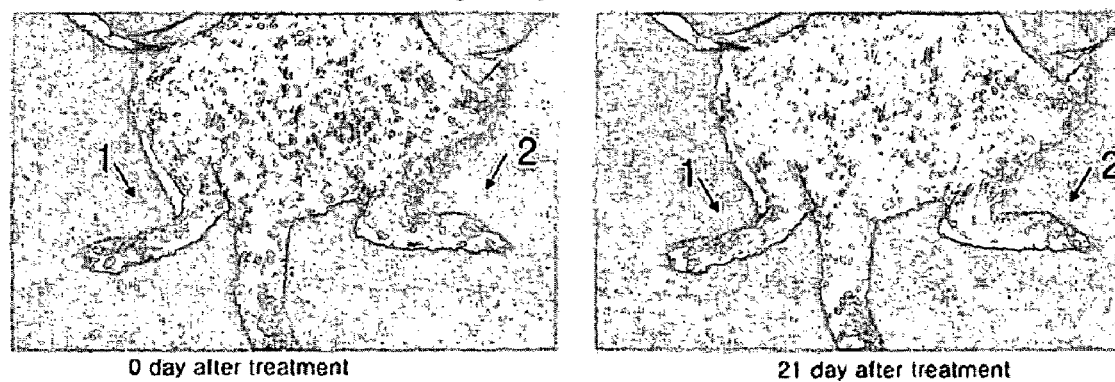
0 day after treatment        21 day after treatment
<RA Score>
1 : Light swelling and flair in joint
2 : Clear swelling and flair in joint
4 : Severe swelling and all over the joint

COMPOSITION COMPRISING NOTOGINSENG RADIX EXTRACT FOR PREVENTING AND TREATING OF ARTHRITIS AS AN EFFECTIVE INGREDIENT

This patent application is a Divisional of U.S. patent application Ser. No. 10/568,257, filed on Feb. 13, 2006, now abandoned which in turn claims the benefit of priority from Korean Patent Application No. 10-2003-0062418, filed on Sep. 6, 2003, through PCT Application Serial No. PCT/KR2004/002255 filed on Sep. 6, 2004, the contents of which are incorporated herein by reference.

FIELD OF THE INVENTION

The present invention relates to a composition comprising Notoginseng radix extract for preventing and treating arthritis as an effective ingredient.

BACKGROUND

Arthritis related diseases are the representative degenerative intractable diseases, which give 12% of total earth population pain. And over 2 million people are suffering from such diseases in Korea.

Arthritis is the general term for symptoms over all the musculoskeletal system caused by inflammatory changes in musculoskeletal and connective tissues. The disease is characterized by chronic inflammation causing permanent damage in tissues, deformity, degeneration and troubles by having an effect on joint, bone, cartilage or the spinal cord (Hofbause, L C, Heufelder, A E: The role of osteoprotegerin and receptor activator of nuclear factor kappaB ligand in the pathogenesis and treatment of rheumatoid arthritis, Arthritis and Rheumatism 44:253-259, 2001).

Arthritis is classified into degenerative arthritis (osteoarthritis), rheumatoid arthritis, non-joint rheumatism or collagen disease.

Degenerative arthritis, which is the most common of all arthritis related diseases, is developed by local degeneration by the worn-out of joint cartilage. The cause of the disease is still unclear but aging or over-weight might be the reason. Primarily, degenerative changes appear in joint cartilage. Degeneration first begins in joint cartilage and kills chondrocytes and then cartilage matrix is destroyed by cathepsin B, cathepsin D, collagenase, etc. The destruction outpaces the generation of proteoglycan and collagen, and adaptability of cartilage to outside force becomes weaker, resulting in microfractures in subchondral bone tissues. As the disease progresses, the hardening of subchondral bone, over-ossification around joint, joint deformation, etc. are observed. Then, the surface of cartilage becomes rough and inflammation in joint cavity enveloped by joint capsule repeats, resulting in constant pain, ankylosis and gradual motor disturbance in joint.

Rheumatoid arthritis is a chronic inflammatory disease over the whole body and its symptoms occur symmetrically to movable joints. The disease is also known as an autoimmune disease caused by malfunction of immune system. However, the cause of the disease is still in question. Rheumatoid arthritis is characterized by continuous inflammatory synovitis causing the destruction of cartilage and bone erosion, resulting in deformity of joint structure. Symptoms of rheumatoid arthritis are joint edema, joint tenderness, inflammation, morning stiffness and acute pain with bending. As the disease progresses, structural damage can be found such as bone erosion and joint destruction (Firestein, G S: Evolving concept of rheumatoid arthritis. Nature 423:356-361, 2003). In addition, a patient with rheumatoid arthritis might suffer from other symptoms by additional organ damage, for example damage of skin, kidney, heart, lung, central nervous system and eye, which is resulted from vasculitis related to autoimmune process.

Arthritis related symptoms include acceleration of erythrocyte sedimentation rate and increase of the concentration of serum C-reactive protein (CRP) or soluble IL-2 receptor (IL-2r). The acceleration of erythrocyte sedimentation rate is detected in almost every active rheumatoid arthritis patients. The concentration of serum C-reactive protein also increases in those patients. It is related to the activation of the disease and the possibility of progressive joint damage. The concentration of soluble IL-2r, a product of T-cell activation, increases in serum and synovial fluid of active rheumatoid arthritis patients, too (Udagawa, N., Kotake, S., Kamatani, N., Takahashi, N., and Suda, T: The molecular mechanism of osteoclastogenesis in rheumatoid arthritis. Athritis Research 4:281-289, 2002).

It is generally believed that Th1 type CD4+T cells play an important role in the progress and continuation of rheumatoid arthritis. That is, CD4+T lymphocytes stimulate macrophages and synovial cells to have inflammatory cytokines (TNF-$\alpha$, IFN-$\gamma$, GM-CSF, IL-2, IL-6) and matrix metalloproteinase secreted, for which signals were transmitted by soluble materials such as interferon-gamma (IFN-$\gamma$) and IL-17 and by cell surface component such as CD69. The secreted cytokines stimulate the proliferation of synovial membrane to form a pannus and destroy cartilage in cooperation with matrix metalloproteinase. The activated CD4+ T cells induce the activation of B cells through the contact with them on cell surface by CD40L, CD28, and a1b2 integrin, leading to the production of antibody containing rheumatoid factors. When CD4+ T cells are activated, osteoprotegerin ligand is expressed on the surface, which stimulates osteoclastogenesis, an important factor for bone destruction (Kong Y Y, Feige U, Sarosi I., et al.: Activated T cells regulate bone loss and joint destruction in adjuvant arthritis through osteoprotegerin ligand. Nature 402, 304-309, 1999). The activated macrophages and fibroblasts accelerate angiogenesis by secreting VEGF, FGF, etc. The activated vascular endothelial cells in synovial membrane make an amplified cycle of inflammation by secreting chemokine such as IL-8, inducing the expression of adhesion molecule and speeding up the infiltration of inflammatory cells. Rheumatoid arthritis is also believed to be a T-cell mediated autoimmune disease, which is related to the antigen-nonspecific intracellular interaction between T-lymphocytes and antigen-presenting cells. The reaction size of T-cells is determined by simultaneous stimuli induced by the interaction between a T-cell surface molecule and its' ligand. A major simultaneous stimulus signal is given by the interaction between T-cell surface receptors, QD28 and CTLA4, and their ligands such as B7-related molecules on antigen-presenting cells, that is CD80 (B7-1) and CD86 (B7-2) (Linsley, P. and Ledbetter, J.: The role of the CD28 receptor during T cell responses to antigen. Ann. Rev. Immunol. 11:191-212, 1993). T-cell activation without simultaneous stimuli results in anergic T-cell response, indicating that immune system does not response to a stimulus [Schwartz, R. H.: Costimulation of T lymphocytes: the role of CD28, CTLA-4, and B7/BB1 in interleukin-2 production and immunotherapy. Cell 71:1065-1068, 1992].

Fundamental treatment of arthritis to cure the cause is still far, and all the medicines developed so far are just for relieving a pain, inhibiting inflammation or keeping the function as it is. Such medicines are supposed to be administered for a long time, but long-term administration of those drugs cause side effects in gastrointestinal system, central nervous system, hematopoietic organ, kidney, liver, etc. (Langenegger T, Michel B A.: Drug treatment for rheumatoid arthritis. Clin Orthop. 366:22-30. 1999).

As explained hereinbefore, arthritis related diseases are considered to be chronic inflammatory diseases and T-cell medicated immune system disorders, so that it is an urgent need, for the treatment of such diseases, to develop a medicine to inhibit release of cytokine and to destroy activated T cells selectively.

The present inventors have made every effort to find out a material from herb medicines that can inhibit release of cytokine and destroy activated T-cells only. And the present inventors have completed this invention by confirming that Notoginseng radix extract can inhibit separation of cytokine and destroy activated T-cells only.

SUMMARY OF THE INVENTION

It is an object of the present invention to provide a composition comprising Notoginseng radix extract for preventing and treating arthritis as an effective ingredient.

BRIEF DESCRIPTION OF THE DRAWINGS

The application of the preferred embodiments of the present invention is best understood with reference to the accompanying drawings, wherein:

FIG. 1 is a schematic diagram showing the method for extracting and separating Notoginseng radix extract of the present invention, FIG. 2 is a graph showing the effect of Notoginseng radix extract of the present invention on release of tumor necrosis factor-alpha (TNF-α), FIG. 3 is a graph showing that Notoginseng radix extract of the present invention destroys activated T-cells selectively, FIG. 4 is a graph showing the inhibiting effect of Notoginseng radix extract of the present invention on the arthritis progress tested by using animals with type 2 collagen induced arthritis, which is presented by arthritis index, FIG. 5 is a set of photographs showing the inhibiting effect of Notoginseng radix extract of the present invention on the arthritis progress tested by animals with type 2 collagen induced arthritis.

DETAILED DESCRIPTION OF PREFERRED EMBODIMENTS

In order to achieve the above object, the present invention provides a composition comprising Notoginseng radix extract for preventing and treating arthritis as an effective ingredient.

The composition of the present invention includes a pharmaceutical composition for preventing and treating arthritis and a composition for health food.

Notoginseng radix extract of the present invention inhibits release of tumor necrosis factor-alpha (TNF-α) and is the death of activated T-cells selectively, so that it can be effectively used for the production of improved health food or the development of a medicine for preventing and treating arthritis.

Here in after, the present invention is described in detail.

Notoginseng radix is a root of a perennial herb belonging to *Panax notoginseng* (Burk.) F. H. Chen. It is smaller than a ginseng and has 7 pieces of leaves. Its' root is in a small thread drum shape and it is raised widely in Yunnan and Sichuan, southern China. Since the plant has 7 leaves on three branches, it has been called 'Samchil (three-seven)' and often called 'Samchil ginseng' owing to its similar appearance to Korean ginseng. The root has 3-8% saponin and its' major components are ginsenoside Rb1, Rg1 and Re, and notoginsenoside R1, R2, Fa and Fc, but small amount of ginsenoside R2, b2, d, e, c are also included. R0 is not contained or if it is, it must be least. Essential oil composition is fewer in Notoginseng radix than in Panax ginseng. Notoginseng radix additionally includes oleanolic acid. Its' root has hemostatic and cardiotonic activities. It was confirmed from animal tests that the root has efficacy of increasing blood flow of coronary artery, decreasing oxygen consumption of cardiac muscle and lowering the levels of lipid and cholesterol in blood. Notoginseng radix also has functions of anti-inflammation, analgesia and hemostasis, so that it is very useful for the treatment of not only inflammatory diseases including hepatitis but also bleeding from trauma, cut, etc, and internal hemorrhage. Applying to a wound or oral administration give the same effects.

Notoginseng radix extract of the present invention is extracted by using water, alcohol or a mixed solvent of water and alcohol. At this time, alcohol is preferred to be ethanol. Conventional extraction methods including cold precipitation, hot precipitation, heating, etc, using the solvent mentioned above are used.

Notoginseng radix extract of the present invention inhibits release of tumor necrosis factor-alpha (TNF-α), so that it can be used for the production of health food or a medicine for preventing and treating arthritis.

In order to investigate how Notoginseng radix extract of the present invention worked to inhibit release of tumor necrosis factor-alpha (TNF-α), THP-1 cells, a human monocytic cell line, were treated with lipopolysaccharide (LPS) and Notoginseng radix extract of the present invention at the concentration of 2 or 10 µl/ml. Then, the amount of released tumor necrosis factor-alpha (TNF-α) in cell culture medium was measured by ELISA. As a result, the amount of released tumor necrosis factor-alpha (TNF-α) was remarkably decreased by the treatment of 10 µl/ml of Notoginseng radix extract of the present invention (see Experimental Example 1).

Notoginseng radix extract of the present invention can be used for the production of health food or a medicine for preventing and treating arthritis owing to its ability to death activated T-cells selectively.

In order to investigate whether or not Notoginseng radix extract of the present invention was able to death activated T-cells only, a lymph node of a 5-week-old female mouse was taken and single cells were prepared. The cells were cultured, during which T cells were activated. The apoptosis of activated T-lymphocytes was investigated. As a result, when cells were treated with over 5 µl/ml of Notoginseng radix extract of the present invention, only activated T-cells were killed (inactivated T-cells were still alive) (see Experimental Example 2).

Notoginseng radix extract of the present invention also inhibits the progress of the disease in animals having type 2 collagen induced arthritis.

In order to investigate the treatment effect on arthritis of Notoginseng radix extract of the present invention, collagen suspension was intra-dermally injected in tail head of a mouse to induce arthritis. Notoginseng radix extract of the present invention was orally administered to the mouse with arthritis, which was then observed. As a result, the progress of arthritis was remarkably inhibited from the 9$^{th}$ day after oral administration of the extract (see Experimental Example 3).

A composition of the present invention can additionally include, in addition to Notoginseng radix extract, one or more effective ingredients having a similar to or the same function as Notoginseng radix extract.

A composition of the present invention can additionally include, in addition to Notoginseng radix extract, one or more effective ingredients having a different function from that of Notoginseng radix extract.

A composition of the present invention can contain at least one of pharmaceutically acceptable carriers, in addition to the above effective ingredients, for the convenience of the administration. Pharmaceutically acceptable carriers can be selected from a group consisting of saline, sterile water, Ringer's solution, buffered saline, dextrose solution, maltodextrin solution, glycerol, ethanol and a mixture of them (one or more components). If necessary, other additives such as anti-oxidants, buffers, fungistats, etc, can be included. A composition of the present invention can also be prepared in the forms of pills, capsules, granules, tablets and injectable solutions such as acqueous solutions, suspensions, emulsions, etc, produced by being mixed with generally used diluents, disintegrating agents, surfactants, binders and lubricants. Besides, a composition of the present invention can be prepared in different forms considering a disease and included ingredients by general method well-known to the people in this field or the method described in Remington's Pharmaceutical science (Newest edition), Mack Publishing Company, Easton Pa. Calcium or vitamin $D_3$ can be added to a composition of the present invention to enhance its medicinal effect of preventing and treating arthritis.

The administration method of a composition of the present invention varies from the purpose of the treatment; either oral administration or parenteral administration (for example, intravenous, intradermal, intraperitoneal or local injection) is fine. And the dosage of the composition is determined according to weight, age, gender, health condition of a patient, diet, administration times and method, excretion rate, and severity of a disease. The effective dosage of Notoginseng radix extract of the present invention is 0.1~10 mg/kg, and 0.1~3 mg/kg is more preferable. The administration times can be once a day or preferably several times a day.

The acute toxicity test in mice via oral administration was performed to see if the Notoginseng radix extract of the present invention has acute toxicity in mice. As a result, its estimated $LD_{50}$ values are much greater than 2 g/kg in mice, indicating that this extract is evaluated to be a safe substance.

A composition of the present invention can be treated for preventing and treating arthritis either independently or in combination with surgical operation, radiotherapy, hormone therapy, chemotherapy and other biological response regulators.

A composition of the present invention can be added to health food to improve arthritis related diseases. Notoginseng radix extract of the present invention can be added to food as it is or together with other food or food ingredients by general method for food process. The mixing ratio of effective ingredients is determined by the purpose of use (for prevention, for promoting health, or for treatment of a disease). In general, Notoginseng radix extract of the present invention is added to food or beverages under 100 weight %, preferably under 50 weight %. However, in the case of long-term administration for the purpose of health and sanitation or health control, the amount of a composition added to food or beverages might be less than the above, but since the composition is safe for human, it could be added more than the above.

There is no limitation in food category applicable to the extract of the present invention. So, the extract can be added to meat, sausages, bread, chocolate, candies, snacks, cookies, pizza, ramyun, noodles, gums, dairy product including ice cream, soups, beverages, tea, drinks, alcoholic drinks and vitamin complex, etc. and other ordinary health food.

A composition for health promoting beverages can additionally include various flavors or natural carbohydrates, like any other ordinary beverages. Natural carbohydrates are exemplified by monosaccharides such as glucose and fructose, disacchsrides such as maltose and sucrose, polysaccharides such as dextrin, cyclodextrin, and sugar alcohols such as xilytole, sorbitol and erythritol. As a sweetening agent, natural sweeteners such as thaumatin and stevia extract, and synthetic sweeteners such as saccharin and aspartame can be used. It is preferred to add natural carbohydrates by 0.1-20 g per 100 ml of a composition of the present invention, and is more preferred to add 1-10 g of natural carbohydrates to 100 ml of the composition.

In addition to the above, a composition of the present invention can also include various nutrients, vitamins, electrolytes, flavoring agents, coloring agents, pectic acid and its salts, alginic acid and its salts, organic acids, protective colloidal thickeners, pH regulators, stabilizers, antiseptics, glycerin, alcohol, carbonating agents used in carbonated beverages, etc. The composition of the present invention can further include sarcocarps to produce natural fruit juices, fruit beverages and vegetable beverages. Each ingredient is used either independently or in combination with others. At this time, the mixing rate is not so important but in general, 0.05-50 parts of weight per 100 parts of weight of the composition of the present invention is preferred.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Notoginseng Radix Extract

Cultivated Notoginseng radix was purchased from a wholesale dried medicinal herb store.

<1-1> Preparation of Notoginseng Radix Crude Extract

<1-1-1> Crude Alcohol Extract of Notoginseng Radix

Notoginseng radix was cut into 1-2 cm fragments. The fragments were washed with running water to eliminate impurities. The fragments were pulverized. 200 g of the Notoginseng radix powder was put in a 3 t flask, which was stirred at reflux at 78.5° C. using 2,000 ml of ethanol. Extraction by heating was repeated three times for 4 hours. The extract was filtered and vacuum-concentrated under reduced pressure by using vacuum rotary evaporator under 40° C., resulting in Notoginseng radix crude extract containing 2.7 g of Notoginseng radix powder (RF1M) (yield: 1.35%).

<1-1-2> Crude Water Extract of Notoginseng Radix

Notoginseng radix crude extract was extracted by the same method as described in the above <1-1-1> and the only difference in the procedure was that water was used instead of ethanol as an extraction solvent.

<1-1-3> Crude Mixed Solvent Extract of Notoginseng Radix

Notoginseng radix crude extract was extracted by the same method as described in the above <1-1-1> and the only difference in the procedure was that a mixed solvent of water (25%) and ethanol (75%) was used instead of ethanol as an extraction solvent.

<1-2> Separation of Notoginseng Radix Crude Extract

A fraction (RF1MB) was obtained from the crude extract (FF1M) prepared in the above <1-1-1> at room temperature by using 500 ml of normal butanol (n-butanol) as a solvent, for which a fraction funnel was used and solvent fractionation was repeated three times.

RF1MB4 fraction was separated from the RF1MB fraction by column chromatography. Column chromatography was performed again with the RF1MB4 fraction, resulting in the final fraction of Notoginseng radix extract (RF1MB4b).

Extraction and separation method of Notoginseng radix extract of the present invention is described in FIG. 1.

In experimental examples of the invention, the final extraction of Notoginseng radix extract (RF1MB4b) was concentrated and then freeze-dried. The dried fraction was diluted with water and used for in vitro and animal tests.

Experimental Example 1

Inhibition of the Release of TNF-α by Notoginseng Radix Extract of the Present Invention Following experiments were performed to investigate whether or not Notoginseng radix extract of the present invention inhibited the release of TNF-α, a cytokine separated from human monocytic cell line 'THP-1 cell'.

<1-1> Cell Selection and Culture

The below cell line was used to investigate the effect of Notoginseng radix extract of the present invention on the release of TNF-α.

Human originated cell line THP-1 (ATCC No. TIB-202) was purchased from ATCC (Rockville, USA) and cultured in RPMI 1640 (Gibco, BRL, USA) medium supplemented with 10% FBS (fetal bovine serum).

<1-2> Quantification of Released TNF-α

In order to investigate the effect of Notoginseng radix extract of the present invention on the release of TNF-α, the amount of released TNF-α was measured by ELISA using cells prepared in the above <1-1>.

Cells were plated into a 96-well plate by $5 \times 10^5$ cells/ml and lipopolysaccharide (LPS) was added in order to activate cells for the release of TNF-A.

An experimental group was treated with Notoginseng radix extract (RF1MB4b) at the concentration of 2 or 10 μl/ml together with LPS. After the treatment, the released TNF-α in culture supernatant was quantified by ELISA.

The results are presented in FIG. 2.

As shown in FIG. 2, when an experimental group was treated with low concentration (2 μl/ml) of Notoginseng radix extract (RF1MB4b), the amount of released TNF-α of the experimental group was just a little different from that of a control group not treated with the extract. But, when the extract was provided with high concentration (10 μl/ml), the amount of released TNF-α in the experimental group was greatly decreased, comparing to a control group.

Thus, the above results indicate that Notoginseng radix extract of the present invention inhibits the release of TNF-α.

Experimental Example 2

Selective Apoptosis of Activated T-Cells by Notoginseng Radix Extract of the Present Invention In order to confirm whether or not Notoginseng radix extract of the present invention could destroy activated T-cells only, following experiments were performed.

<2-1> Separation and Activation of T-Cells

A lymph node of a 5-week-old female mouse was taken out and mashed by the back tip of a sterilized syringe to extract cells. The cells were filtered by a cell-filter (Falcon, N.J. USA) and washed with PBS, then put in a culture medium at the concentration of $2 \times 10^6$ cells/ml. As a culture medium, RPMI 1640 (Gibco, BRL, USA) supplemented with 10% FBS (fetal bovine serum) was used.

In order to activate T-cells only, concanavalin A was added by 5 μg/mL to the medium, followed by culture for 48 hours. After 48 hours of culture, 10 mg/ml of methyl-α-D-mannopyranoside (sigma, Germany) was put in the medium, followed by further culture for 30 minutes. Then, the cells were washed with PBS three times and put in a culture medium supplemented with 100 units/ml of human interleukine-2 (hIL-2, R&D, Minnesota, USA), followed by further culture for 48 hours and cell density was maintained as $2 \times 10^6$ cells/ml during the culture (Lenardo M J. et al.: Interleukin-2 programs mouse alpha beta T lymphocytes for apoptosis. Nature. 353(6347):858-61. 1991).

<2-2> Investigation of Selective Apoptosis of Activated T-cells

The concentration of activated T-cells was adjusted to $1 \times 10^6$ cells/ml., then they were put in a 96-well plate (Falcon, USA) by 200 μl/well. At that time, 100 units/ml of human interleukine-2 (hIL-2) was added to each well.

While a control group was not treated with Notoginseng radix extract, an experimental group was treated with the final fraction (RF1MB4b) of Notoginseng radix extract prepared in the above example at different concentrations (5 μg/ml, 10 μg/ml, 20 μg/ml) before being cultured for 24 hours.

As a control, inactivated cells were prepared as follows.

Single cells were collected from spleen and cell density was adjusted to $2 \times 10^6$ cells/ml, which were distributed to a 96 well plate by 200 μl/well. Notoginseng radix extract was added thereto, followed by culture for 24 hours. After 24 hours of culture, the cells were transferred to a flow tube, to which propidium iodide (PI) was added. Then, live cells were counted for 20 seconds by using CellQuest program of FACSCaliver (Becton Dickinson, France).

Apoptosis was calculated as follows: (1−F extract treated cells/untreated cells)×100. All candidate drugs were examined by that math formula to choose a drug to induce high apoptosis of activated T-cells but low apoptosis of naive T-cells (Sabapathy K, Hu Y, Kallunki T, Schreiber M, David J P, Jochum W, Wagner E F, Karin M.: JNK2 is required for efficient T-cell activation and apoptosis but not for normal lymphocyte development. Curr Biol. 11;9(3):116-25. 1999).

The results are presented in FIG. 3.

As shown in FIG. 3, when Notoginseng radix extract of the present invention was treated with high concentration over 5 μl, activated T-cells were selectively destroyed while inactivated T-cells still remained.

Thus, it was confirmed that Notoginseng radix extract of the present invention destroys activated T-cells selectively and the apoptosis effect was concentration-dependent.

Experimental Example 3

Inhibition of the Progress of Arthritis in Test Animals with Type 2 Collagen Induced Arthritis by Notoginseng Radix Extract of the Present Invention In order to investigate whether or not Notoginseng radix extract of the present invention could inhibit the progress of arthritis in test animals having type 2 collagen induced arthritis, following experiments were performed.

<3-1> Inducement of Arthritis in Test Animals

In order to prepare test animals having type 2 collagen induced arthritis, 5-6 week old male DBA1 mice were purchased from SCI company, Japan, and the mice were raised at 21° C. with 40% humidity.

Bovine type 2 collagen (Condrex Co., Japan) was dissolved in 0.05% acetic acid, making the concentration 2 mg/ml. Then the type 2 collagen was mixed with the same amount of complete adjuvant (Condrex Co., Japan). While cooling down with ice, the mixture became homogeneous suspension by using T-connector linked to 3 ml syringe. After confirming the suspension was prepared rightly, tail head of a mouse was sterilized with alcohol cotton and 100 µl of collagen suspension was injected under the skin of the tail head.

<3-2> Oral Administration of Notoginseng Radix Extract (RF1MB4B) of the Present Invention Notoginseng radix extract (RF1MB4b) prepared in the above example was dissolved in water, resulting in 2.5 mg/ml solution. The solution was filtered by 0.25 uM filter.

The filtered solution was diluted to 0.2 mg/ml and was administered to the mouth of a mouse through sonde linked to a 1 ml syringe, once a day and by 0.05 mg/250 µl/mouse.

<3-3> Progress of Arthritis: Naked Eye Observation and Diagnosis

In order to investigate arthritis treating effect of Notoginseng radix extract (RF1MB4b) of the present invention, the Notoginseng radix extract (RF1MB4b) prepared in the above example was administered by the same method as described in the above <3-2> to test animals having arthritis induced by the injection of collagen suspension.

Arthritis was developed 30 days after collagen suspension was injected to a mouse. Naked eye observation on lesion of arthritis was performed by using following scores based on literature cited.

0: No swelling or flair, 1: Light swelling and flair in joint, 2: Clear swelling and flair in joint, 3: Severe swelling and flair in joint including knuckle joint, 4: Severe swelling in all over the joint.

Therefore, the highest score of lesion of arthritis is 16 per mouse, which sums up scores of forelegs and hind legs, and the highest score per one leg is 4 (Courtenay J S, Dallman M J, Dayan A D, et al.: Immunization against heterologous type II collagen induces arthritis in mice. Nature 283: 666-668. 1980).

FIG. 4 and FIG. 5 present the results of investigation, after oral administration of the extract, of arthritis progress inhibiting effect of Notoginseng radix extract of the present invention in test animals with type 2 collagen induced arthritis.

In FIG. 4, the arthritis progress inhibiting effect of Notoginseng radix extract of the present invention in test animals with type 2 collagen induced arthritis was presented as arthritis index, and FIG. 5 is a set of photographs showing the arthritis progress inhibiting effect of Notoginseng radix extract of the present invention in animals having type 2 collagen induced arthritis.

As shown in FIG. 4, when Notoginseng radix extract of the present invention was orally administered into a mouse having type 2 collagen induced arthritis, the progress of the disease was obviously inhibited from the $9^{th}$ day of administration, comparing to a control group.

As shown in FIG. 5, both a control medicine without Notoginseng radix extract and an experimental medicine including the extract were orally administered respectively to mice having type 2 collagen induced arthritis. Big difference between the two was observed after 21 days from the administration. A mouse treated with a control medicine showed very severe swelling all over the joints but a mouse administered with an experimental medicine just showed light flair and swelling in joints.

Therefore, it was confirmed that Notoginseng radix extract of the present invention effectively inhibits the progress of arthritis.

Example 4

Acute Toxicity Test with Notoginseng Radix Extract of the Present Invention

Notoginseng radix extract of the present invention is classified into a food material, indicating that it is safe. But, for the use as a treatment medicine, acute toxicity of the extract had to be investigated as follows.

6-week old SPF mice were used in the tests for acute toxicity. Notoginseng radix extract (RF1MB4b) prepared in the above example was suspended in distilled water and orally administered once to 5 mice per group at the dosage of 2, 1, and 0.5 g/kg.

Death, clinical symptoms, and weight change in mice were observed, hematological tests and biochemical tests of blood were performed, and any abnormal signs in the gastrointestinal organs of chest and abdomen were checked with eyes during autopsy.

The results showed that Notoginseng radix extract of the present invention did not cause any specific clinical symptoms, weight change, or death in mice. No change was observed in hematological tests, biochemical tests of blood, and autopsy.

Notoginseng radix extract (RF1MB4b) of the present invention used in this experiment is evaluated to be safe substance since it does not cause any toxic change in mice up to the level of 2 g/kg and its estimated $LD_{50}$ values are much greater than 2 g/kg in mice.

Manufacturing Example 1

Preparation of Pharmaceutical Formulations

| <1-1> Preparation of powders | |
|---|---|
| Notoginseng radix extract | 2 g |
| Lactose | 1 g |

Powders were prepared by mixing all the above components and filled airtight bag with them.

| <1-2> preparation of tablets | |
|---|---|
| Notoginseng radix extract | 100 mg |
| Corn starch | 100 mg |
| Lactose | 100 mg |
| Magnesium stearate | 2 mg |

Tablets were prepared by mixing all the above components by the conventional method for preparing tablets.

| <1-3> Preparation of capsules | |
|---|---|
| Notoginseng radix extract | 100 mg |
| Corn starch | 100 mg |
| Lactose | 100 mg |
| Magnesium stearate | 2 mg |

Capsules were prepared by mixing the components above and filled gelatin capsules with them according to the conventional method for capsules.

Manufacturing Example 2

Preparation of Food

Foodstuff containing Notoginseng radix extract of the present invention was prepared as follows.

<2-1> Preparation of Cooking Spices

Health improving spices and condiments containing Notoginseng radix extract of the present invention by 20-95 weight % were prepared.

<2-2> Preparation of Tomato Ketchup and Sauce

Health improving tomato ketchup or sauce was prepared by adding Notoginseng radix extract of the present invention by 0.2-1.0 weight % to original tomato ketchup or sauce.

<2-3> Preparation of Flour Food

Health improving flour food was prepared by adding Notoginseng radix extract of the present invention by 0.5-5.0 weight % to wheat flour and then making the flour into bread, cakes, cookies, crackers and noodles.

<2-4> Preparation of Soups and Gravies

Notoginseng radix extract of the present invention was added by 0.1-5.0 weight % to soups and gravies to produce health improving processed meats, noodle soups and gravies.

<2-5> Preparation of Ground Beef

Notoginseng radix extract of the present invention was added by 10 weight % to ground beef to prepare health improving ground beef.

<2-6> Preparation of Dairy Products

Notoginseng radix extract of the present invention was added by 5-10 weight % to milk to prepare health improving dairy products such as butter, ice cream, etc.

<2-7> Preparation of Sunsik

Brown rice, barley, glutinous rice and coix; (job's tear) were gelatinizated by the conventional method, followed by drying. The dried mixture was distributed and pulverized, resulting in 60-mesh grain size of powders.

Black bean, black sesame and perilla were steamed and dried by the conventional method. The dried mixture was distributed and pulverized, resulting in 60-mesh grain size of powders.

Notoginseng radix extract of the present invention was vacuum-concentrated under reduced pressure using a vacuum concentrator, which was then spray-dried with a hot-air drier. The dried material was pulverized by a grinder, resulting in 60-mesh grain size of powders.

The prepared grain, seeds, and dried Notoginseng radix extract powders were all mixed at the following ratio.

Grain (brown rice 30 weight %, coix 15 weight %, barley 20 weight %),

Seeds (perilla 7 weight %, black bean 0.8 weight %, black sesame 7 weight %),

Dried powder of Notoginseng radix extract (3 weight %),

Ganoderma lucidum (0.5 weight %),

Rehmannia glutinosa (0.5 weight %)

Manufacturing Example 3

Preparation of Beverages

<1-1> Preparation of Carbonated Beverages

Sugar (5-10%), citric acid (0.05-0.3%), caramel (0.005-0.02%) and vitamin C (0.1-1%) were mixed, to which purified water (79-94%) was added to make syrup. The prepared syrup was sterilized at 85-98% for 20-180 seconds, then mixed with cooling water at the ratio of 1:4. Then, carbon dioxide gas (0.5-0.82%) was given to the mixture to prepare carbonated beverages containing Notoginseng radix extract of the present invention.

<1-2> Preparation of Health Beverages

Acid fructose (0.5%), oligosaccharide (2%), sugar (2%), salt (0.5%) and water (75%) were all mixed with Notoginseng radix extract evenly, followed by sterilization. The mixture was put in a small container such as a glass bottle or pat bottle, resulting in health beverages.

<1-3> Preparation of Vegetable Juice 5 g of Notoginseng radix extract of the present invention was added to 1,000 ml of tomato or carrot juice to prepare health vegetable juice.

<1-4> Preparation of Fruit Juice 1 g of Notoginseng radix extract of the present invention was added to 1,000 ml of apple or grape juice to produce health fruit juice.

INDUSTRIAL APPLICABILITY

As explained hereinbefore, Notoginseng radix extract of the present invention has activities of inhibiting TNF-α release and destroying activated T-cells selectively.

Therefore, Notoginseng radix extract of the present invention can be effectively used for the production of health food or a medicine for preventing and treating arthritis.

What is claimed is:

1. A method for treating arthritis in a subject, identified as in need of treatment of arthritis comprising,
   (i) obtaining a crude extract of Notoginseng radix by extracting Notoginseng radix with water, ethanol or a mixed solvent thereof;
   (ii) isolating an n-butanol fraction by fractioning said crude extract obtained from step (i) with n-butanol; and (iii) administering to the subject a therapeutically effective amount of a composition comprising the n-butanol fraction of Notoginseng radix obtained from step (ii).

2. The method according to claim 1, wherein the administering comprises administering orally or administering parenterally.

3. The method according to claim 1, wherein the composition is a pharmaceutical composition which comprises the n-butanol fraction of Notoginseng radix as a therapeutically effective ingredient.

4. The method according to claim 3, wherein the pharmaceutical composition is in form of powders, tablets or capsules.

5. The method according to claim 1, wherein the composition is a food composition which comprises the n-butanol fraction of Notoginseng radix as an effective ingredient.

6. The method according to claim 5, wherein the food composition is a foodstuff selected from the group consisting of cooking spices, tomato ketchup, flour food, processed meats, noodle soups, gravies, ground beef, dairy products and sunsik.

7. The method according to claim 1, wherein the therapeutically effective amount of the composition is from 0.1 to 10 mg/kg.

8. The method according to claim 7, wherein the therapeutically effective amount of the composition is from 0.1 to 3 mg/kg.

9. The method according to claim 1, wherein the subject is a human being.

* * * * *